United States Patent [19]
Forte

[11] Patent Number: 5,092,897
[45] Date of Patent: Mar. 3, 1992

[54] IMPLANTABLE ACETABULAR PROSTHETIC HIP JOINT WITH UNIVERSAL ADJUSTABILITY

[76] Inventor: Mark R. Forte, 11 Oak La., Pine Brook, N.J. 07058

[21] Appl. No.: 494,153

[22] Filed: Mar. 15, 1990

[51] Int. Cl.⁵ .............................................. A61F 2/32
[52] U.S. Cl. .................................................... 623/22
[58] Field of Search ............................. 623/22, 18, 23

[56] References Cited

U.S. PATENT DOCUMENTS

| | | |
|---|---|---|
| 3,818,512 | 8/1974 | Shersher . |
| 4,678,472 | 7/1987 | Noiles . |
| 4,871,368 | 10/1989 | Wagner ................................ 623/22 |
| 4,919,674 | 4/1990 | Schelhas .............................. 623/22 |

*Primary Examiner*—David J. Isabella
*Attorney, Agent, or Firm*—Klauber & Jackson

[57] ABSTRACT

An implantable prosthetic hip joint includes an acetabular shell component for securing the prosthetic joint within the acetabulum socket of a biological hip bone, and including an inner spherical surface, an open circumferential end and a plurality of apertures extending therethrough at the open circumferential end; an annular wedge retaining ring positioned within the acetabular shell component, the ring including a plurality of counter-sunk apertures therein in alignment with the apertures extending through the acetabualr shell component; a hemispherical asymmetric socket insert in the acetabular shell component and including an outer spherical dome engaging the inner spherical surface of the acetabular shell component, an open circumferential end having an asymmetric lip threaeat and an inner spherical surface, the outer spherical dome including a tapered surface for engagement with the wedge retaining ring; a femoral component having a femoral stem connected with the femur of a person and a femoral head connected with the femoral stem and received in the inner spherical surface of the socket insert for ball-and-socket movement therein; and a plurality of screws inserted through the apertures of the wedge retaining ring and acetabular shell component and threadedly received within the hip bone so as to force the wedge retaining ring inwardly to compress the socket insert and retain the same within the acetabular shell component in a fixed position, and loosening of these screws permits universal rotational adjustment of the socket insert in the acetabular shell comoponent.

13 Claims, 8 Drawing Sheets

IMPLANTABLE ACETABULAR PROSTHETIC HIP JOINT WITH UNIVERSAL ADJUSTABILITY

BACKGROUND OF THE INVENTION

This invention relates generally to prosthetic devices, and more particularly, is directed to an acetabular prosthetic hip joint assembly with universal adjustability.

Each hip joint in the human body includes an acetabulum or natural socket in the pelvis that receives the femoral head or ball, which is joined to the femur or thigh bone by a neck portion. As a result, a ball-and-socket joint is provided. In many instances, however, total hip joint replacement may be required. For example, due to various progressive deteriorative diseases, such as osteoarthritis, or abnormal stresses applied to the hip joint, the hip joint, and particularly the femur neck, may fail. In some cases, only the femoral head and neck require replacement, while in other cases, the acetabulum must also be replaced.

Various hip joint prostheses have been proposed. Generally, an acetabular shell component or cup is cemented or press fit into the acetabulum socket in the bone. A femoral member comprising an elongated stem, a neck and a head are mounted to the femur by cementing or press fitting the stem into the intramedullary canal of the femur. The femoral head is then received in a socket insert fixedly secured within the acetabular shell component to provide a ball-and-socket movement therein. Generally, however, the socket insert, once installed, cannot be removed without destroying the same.

An example of an arrangement in which the socket insert is adjustable, is disclosed and shown in U.S. Pat. No. 4,678,472 to Noiles. The present invention is particularly related to the arrangement in FIGS. 33 and 34 thereof. In order to lock the socket insert to the acetabular shell component, screws pass through external lugs of the socket insert and through holes in the acetabular shell component. A small wedge is provided between the socket insert and the acetabular shell component so that, as the screws are tightened, the wedge is forced inwardly by one of the screws to provide a friction fit between the socket insert and acetabular shell component.

However, due to the use of lugs on the outer peripheral surface of the socket insert, it is necessary to completely remove the screws in order to adjust the angular position of the socket insert in the acetabular shell component. This is cumbersome and burdensome, particularly during an operation on a person. Further, the use of such lugs provides only marginal locking retention and limits the adjustability of the socket insert with respect to the acetabular shell component to only a few angular orientations of the socket face. Often times, however, minute variations are required which could not be obtained with this arrangement. Still further, because of this arrangement in which the wedge is actually fit within the outer wall of the socket insert, the socket insert is formed in two parts, which makes assembly difficult during an operation.

U.S. Pat. No. 3,818,512 to Shersher discloses a hip joint assembly with a symmetrical socket insert held in place within the acetabular shell by means of a self-locking nut threadedly received in the acetabular shell. However, this device, by providing a symmetrical socket insert, is not concerned with the different angular orientations thereof.

OBJECTS AND SUMMARY OF THE INVENTION

Accordingly, it is an object of the present invention to provide an implantable prosthetic hip joint that overcomes the aforementioned problems with the prior art.

It is another object of the present invention to provide an implantable prosthetic hip joint that provides 360 degree adjustability as installed, to provide interoperative selection and evaluation of infinite, or at least numerous, levels of socket flexion and version relative to cup placement within the acetabulum, whereby to achieve maximum hip joint stability.

It is still another object of the present invention to provide an implantable prosthetic hip joint having a high level of retention of the socket insert within the cup.

It is yet another object of the present invention to provide an implantable prosthetic hip joint which provides easy unlocking, removal and/or adjustment of the socket insert without inflicting damage thereto, when positional modification is required.

In accordance with an aspect of the invention, an implantable prosthetic joint includes:

a) first bone securing means for constraining the prosthetic joint within a first bone of a biological joint, the first bone securing means including a spherical shell securable within a socket of the first bone, the shell including an inner spherical surface and an open circumferential end;

b) second bone securing means for securing the prosthetic joint to a second bone of the biological joint, the second bone securing means including a femoral head and stem means connected with the femoral head for securing the prosthetic joint to the second bone;

c) asymmetric socket insert means for connecting the second bone securing means with the first bone securing means, the socket insert means including:
  i) an outer spherical dome which engages with the inner spherical surface of the shell;
  ii) an open circumferential end having an asymmetric lip thereat; and
  iii) an inner spherical surface which receives the femoral head for ball-and-socket movement therein;

d) wedge means, interposed between the socket insert means and the first bone securing means, for releasably securing the socket insert means in a non-rotatable manner with respect to the first bone securing means; and e) securing means, out of engagement with the socket means, for releasably securing the wedge means to the first bone securing means such that the socket insert means is assembled with the first bone securing means in a fixed and immovable manner, while providing infinite angular adjustability of the socket means with respect to the first bone securing means when the securing means releases the wedge means from the first bone securing means.

In accordance with another aspect of the invention, an implantable prosthetic joint includes:

a) first bone securing means for constraining the prosthetic joint within a first bone of a biological joint, the first bone securing means including a spherical shell securable within a socket of the first bone, the shell including an inner spherical surface and an open circumferential end;

b) second bone securing means for securing the prosthetic joint to a second bone of the biological joint, the second bone securing means including a femoral head and stem means connected with the femoral head for securing the prosthetic joint to the second bone;

c) asymmetric socket insert means for connecting the second bone securing means with the first bone securing means, the socket insert means including:
  i) an outer spherical dome which engages with the inner spherical surface of the shell;
  ii) an open circumferential end having an asymmetric lip thereat; and
  iii) an inner spherical surface which receives the femoral head for ball-and-socket movement therein;

d) securing means for securing the socket insert means to the first bone securing means; and e) rotational restraint means for preventing rotational movement of the socket insert means with respect to the first bone securing means when the socket insert means is secured in an operative condition with respect to the first bone securing means, and for permitting rotational movement of the socket insert means with respect to the first bone securing means when the socket insert means is not secured in an operative condition with respect to the first bone securing means, the rotational restraint means including:
  i) first locking means on the socket insert means in facing relation to the spherical shell, and
  ii) second locking means on the spherical shell for mating with the first locking means when the socket insert means is assembled with the first bone securing means in the operative condition.

The above and other objects, features and advantages of the present invention will become readily apparent from the following detailed description thereof which is to be read in connection with the accompanying drawings.

DETAILED DESCRIPTION OF THE PREFERRED EMBODIMENTS

Referring to the drawings in detail, and initially to FIGS. 1–4 thereof, an implantable prosthetic hip joint 10 according to one embodiment of the present invention includes a thin wall acetabular cup or shell component 12 of a substantially hemispherical configuration. Acetabular shell component 12 thereby has an outer spherical surface 14. Preferably, acetabular shell component 12 is fabricated from 6AL4V titanium or a cobalt-chromium alloy, with outer spherical surface 14 being a porous coated surface for improved cement bonding and fixation of acetabular shell component 12 within an acetabulum socket 16 of a hip bone 18. Such porous coated outer spherical surface 14 also provides for cementless tissue ingrowth osseous integration. Generally, the dimensions of acetabular shell component 12 are such as to provide a press-fit securement thereof within acetabulum socket 16.

Figures 3, 5:
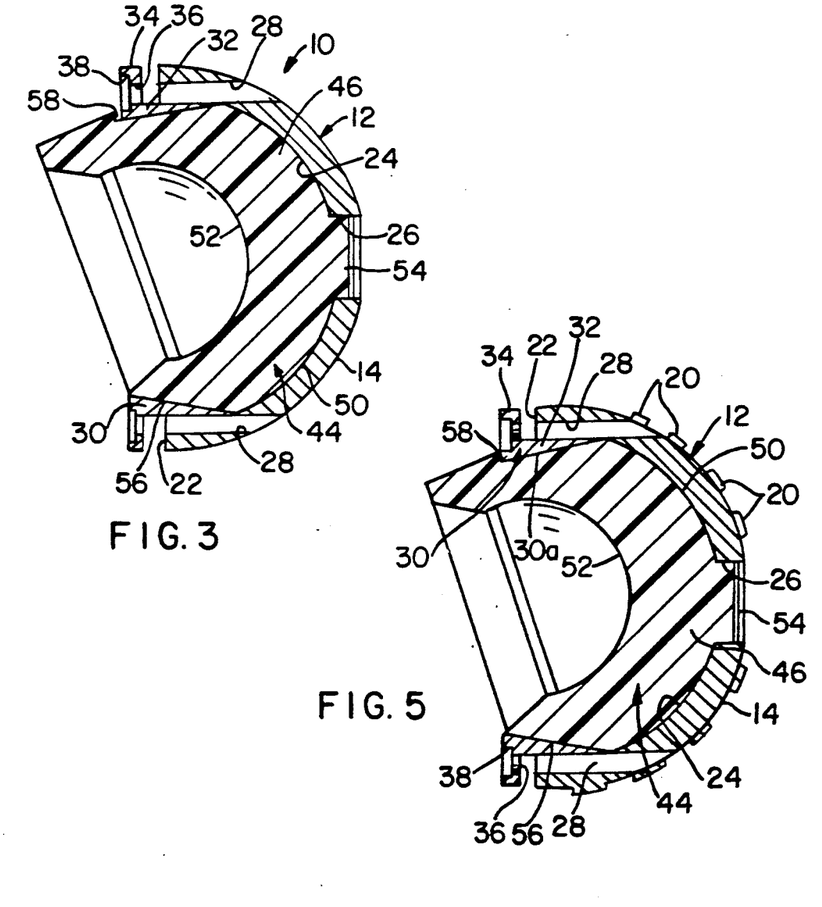
FIG. 3 is a cross-sectional view of the implantable prosthetic hip joint of FIG. 3 in an unassembled condition.
FIG. 5 is a cross-sectional view of an implantable prosthetic hip joint according to another embodiment of the present invention, in an unassembled condition.

Further, as shown in the alternative embodiment of FIG. 5, outer spherical surface 14 can be provided with a series of macro-textured concentric rings 20 or the like for macrostructuring so as to improve component interdigitation with surrounding bone and also to improve the bead/substrate bond strength by allowing the macro-steps to "unload" the beads during imposed shear force loading. Alternatively, a micro-textured porous surface can be provided for component fixation within the acetabulum by biological bone ingrowth.

Figures 1, 2:
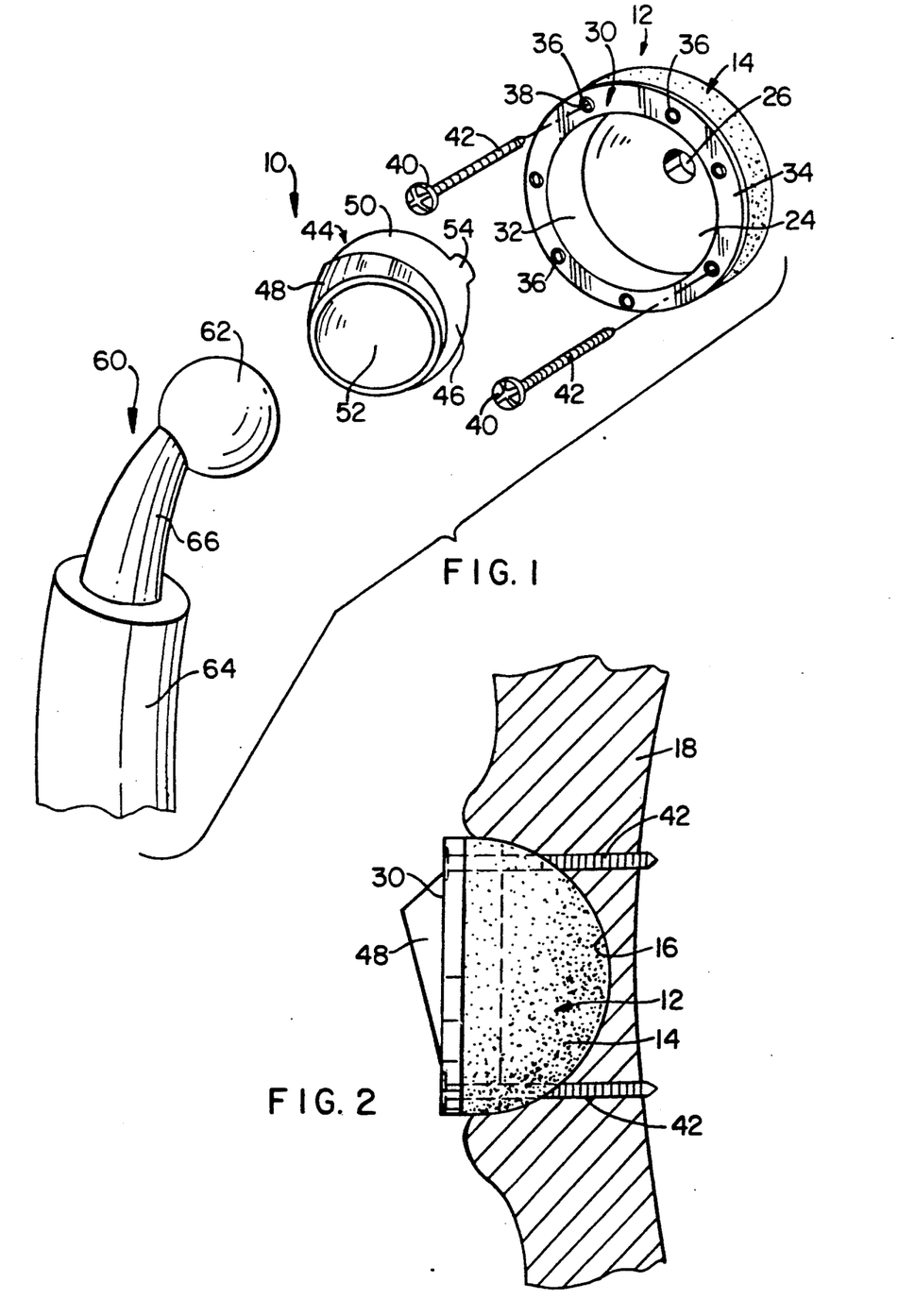
FIG. 1 is an exploded perspective view of an implantable prosthetic hip joint according to one embodiment of the present invention.
FIG. 2 is an elevational view of the implantable prosthetic hip joint of FIG. 1 assembled in a socket of the hip bone.

Acetabular shell component 12 further includes an open circumferential end 22 and an inner spherical surface 24. A central or apical opening 26 preferably extends through the central portion at the rear of acetabular shell component 12. Opening 26 functions to facilitate inspection of the cup/bone interface after component impaction, to provide access for bone graft augmentation behind acetabular shell component 12 and/or to provide an engagement port for the socket insert for improved rotational constraint and assembly stability.

In addition, a plurality of, for example seven, screw holes 28 extend axially through acetabular shell component, starting at open circumferential end 22 and exiting through outer spherical surface 14. Screw holes 28 are preferably equiangularly arranged.

An annular wedge retaining ring 30 is provided within acetabular shell component 12. Specifically, wedge retaining ring 30 includes an annular wedge wall 32 which fits within the inner cylindrical surface of acetabular shell component 12, and has an inner surface 30a. Wedge retaining ring 30 also includes an outer, radially outwardly directed annular flange 34 formed at the outer end of wedge wall 32. Flange 34 sits on open circumferential end 22 of acetabular shell component 12. In addition, flange 34 includes a plurality of, for example seven, screw holes 36 therethrough which are in alignment with screw holes 28 of acetabular shell component 12. Screw holes 36 are preferably countersunk, as at 38 in order to receive the heads 40 of cancellous bone screws 42 that extend through screw holes 36 and 28. It will be appreciated that, when screws 42 extend through screw holes 28 and 36, they extend through the outer spherical surface 14 of acetabular shell component 12 and are threadedly received within the hip or acetabular bone 18, as shown in FIG. 2. In this manner, acetabular shell component 12 is secured to hip bone 18 by both cement or press fit, and screws 42. Screw holes 28 and 36 are preferably compatible with a 5.0 mm cancellous bore screw size. Retaining ring 30 is preferably fabricated of 6AL4V titanium alloy. Wedge retaining ring 30 can be of a split ring construction, but need not be so.

An asymmetric ultra high molecular weight polyethylene (UHMWPE) socket insert 44 is secured within acetabular shell component 12. Specifically, socket insert 44 has a substantially hemispherical main body 46 and an asymmetric lip 48 at the open circumferential end of main body 46, such arrangement being well-known in the art and shown, for example, at FIG. 32 of the aforementioned U.S. Pat. No. 4,678,472 to Noiles, the entire disclosure of which is incorporated herein by reference. Main body 46 includes an outer spherical dome 50 which engages with inner spherical surface 24 of acetabular shell component 12 when assembled, and an inner spherical surface 52. A cylindrical key 54 is provided at the central rear portion of outer spherical dome 50 for insertion within central through hole 26. Accordingly, when socket insert 44 is assembled with acetabular shell component 12, socket insert 44 is only permitted to move rotationally about the axis of cylindrical key 54.

Figure 4:
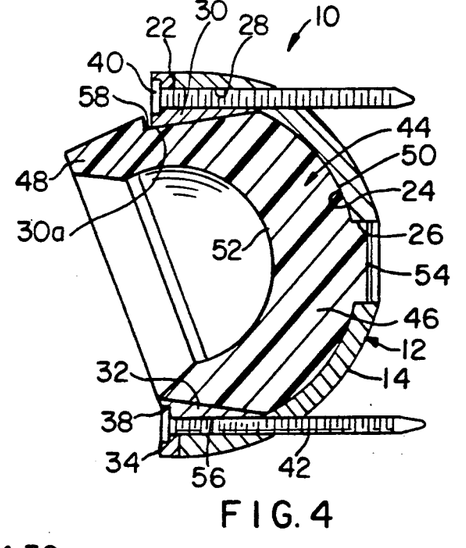
FIG. 4 is a cross-sectional view of the implantable prosthetic hip joint of FIG. 2 in an assembled condition.

As shown best in FIGS. 3 and 4, outer spherical dome 50 is cut-away to provide an annular tapered surface 56 in contact with inner surface 30a and which preferably defines a shoulder 58 with the large width portion of asymmetric lip 48. Tapered surface 56 is provided to mate with the inner surface of annular wedge wall 32 of wedge retaining ring 30 in order to provide a wedging action so as to retain socket insert 44 within acetabular shell component 12.

Initially, after acetabular shell component 12 has been cemented or press fitted within acetabulum socket 16, wedge retaining ring 30 and socket insert 44 are in the positions shown in FIG. 3. Upon tightening of screws 42, which extend through screw holes 28 and 36, into hip bone 18, wedge retaining ring 30 is forced inwardly to the position shown in FIG. 4. As a result, a wedging action is provided with socket insert 44 so as to provide a friction fit between socket insert 44 and acetabular shell component 12, thereby securing socket insert 44 to acetabular shell component 12. Thus, there is sufficient compressive force to retain and lock socket insert 44 and to also provide preloading and associated fixation stability of the shell component/acetabular bone interface.

In addition, prosthetic implantable hip joint 10 includes a femoral component 60 having a ball-shaped femoral head 62 connected to a femoral stem 64 through a neck 66. The free end of femoral stem 64 is connected with the femur (not shown) of a person. Femoral head 62 is received within socket insert 44 so as to form a ball-and-socket joint therewith.

It will be appreciated that the present invention provides distinct advantages over the prior art. In the first place, in order to adjust the angle of relative rotation between socket insert 44 and acetabular shell component 12, it is only necessary to loosen screws 42 so as to relieve the wedging action. In other words, it is not necessary to remove screws 42 entirely. In addition, after screws 42 have been loosened, socket insert 44 can be adjusted or dialed 360 degrees in any angular orientation. Thus, the angular orientation is not limited to a finite number of angular positions, as for example in U.S. Pat. No. 4,678,472 to Noiles. Thus, re-evaluation and repositioning of socket insert 44 can be readily and easily accomplished. Still further, socket insert 44 is constructed from a single piece. Also, since wedge retaining ring 30 is provided as an annular ring, a substantially uniform compressive force is applied to socket insert 44, thereby providing improved frictional engagement therewith.

It will be appreciated that various modifications can be made to the present invention. For example, although seven screw holes 28 and 36 are provided, this number may change. Further, all of such screw holes need not be utilized. Thus, the present invention shows the use of two screws 42. This number may also vary.

Further, the tapered inner face 30a of wall 32 of retaining ring 30 can be machined with a series of circumferential, longitudinal or the like grooves (not shown) to enhance the degree of mechanical interlock. Also, retaining ring 30 can be of a split ring construction to allow ease of engagement with socket insert 44.

Referring now to FIGS. 6-12, an implantable prosthetic hip joint 110 according to another embodiment of the present invention will now be described, in which elements corresponding to those in implantable prosthetic hip joint 10 of FIGS. 1-5 are identified by the same reference numerals with a 100 prefix, and a detailed description of the common elements will be omitted herein for the sake of brevity.

Figures 6, 7, 8, 9, 10:
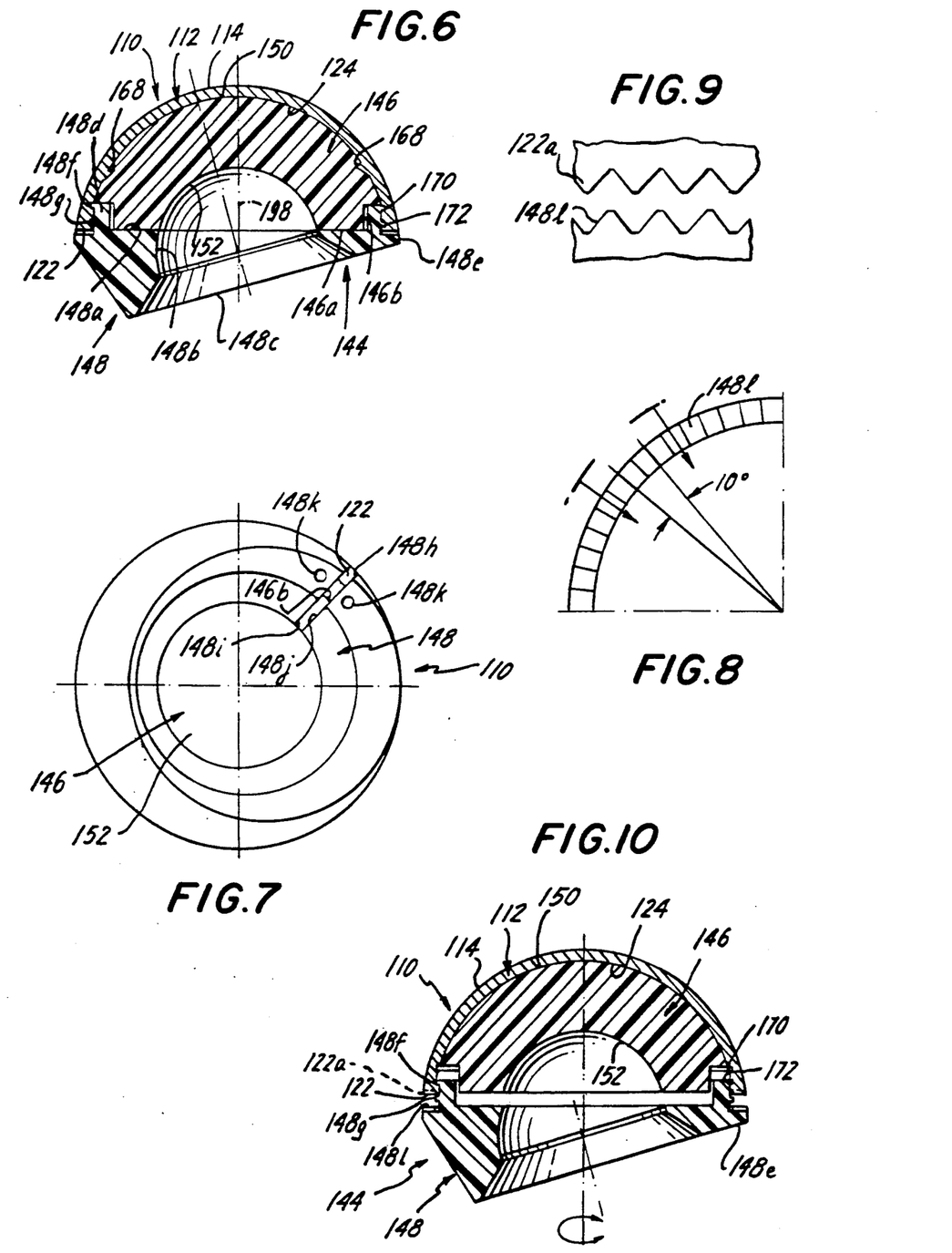
FIG. 6 is a cross-sectional view of an implantable prosthetic hip joint according to another embodiment of the present invention.
FIG. 7 is a bottom plan view of the implantable prosthetic hip joint of FIG. 6.
FIG. 8 is a schematic drawing showing the pitch of the locking splines of the implantable prosthetic hip joint of FIG. 6.
FIG. 9 is an elevational view of the locking splines of FIG. 6.
FIG. 10 is a cross-sectional view similar to FIG. 6, showing the implantable prosthetic hip joint thereof in an inoperative condition.

As shown therein, socket insert 144 is comprised of two sections, namely an upper bearing insert 146 which seats within acetabular shell component 112. Bearing insert 146 has a substantially hemispherical configuration with an outer spherical dome 150 of substantially identical shape and dimensions as inner spherical surface 124 of acetabular shell component 112 so as to seat flush therewith.

A plurality, for example, three or four, of equiangularly spaced ribs, keys, barbs or the like 168, may be formed on inner spherical surface 124. In this manner, when bearing insert 146 is made of a deformable plastic material and is forcibly inserted into acetabular shell component 112, barbs, ribs or the like 168 will cut into bearing insert 146, whereby plastic flow will occur so that bearing insert 146 is restrained in acetabular shell component 112 from pull-out and rotation.

In addition, bearing insert 146 includes an inner spherical surface 152, which is dimensioned to accommodate the femoral head 62 (FIG. 1) for ball-and-socket movement therein. In this regard, bearing insert 146 is preferably fabricated from a molded or machined ultra-high molecular-weight polyethylene (UHMWPE), aluminum oxide ceramic, zirconium oxide ceramic or other comparable material.

It will be appreciated that the outer annular face 146a of bearing insert 146 has a planar configuration.

The second section of socket insert 144 is a lower rim insert 148 which is removably locked to the inner cylindrical surface at the lower end of acetabular shell component 112, at a position below bearing insert 146 and having an inner planar surface 148a in flush contact with outer face 146a of bearing insert 146 so as to ensure that bearing insert 146 is locked in the position shown in FIG. 6. As will be described in detail hereinafter, rim insert 148 is mobile and can be rotated to different positions relative to bearing insert 146 and, in this regard, rim insert 148 includes an inner bearing surface 148b which forms a continuation of inner spherical surface 152 with the same geometry. Rim insert 148 has an asymmetric outer socket face 148c relative to the axis 198 of the acetabular shell component 112 and upper bearing insert 146. Socket face orientation can thus be adjusted by merely rotating asymmetrical rim insert 148, relative to symmetrical bearing insert 146.

An outer peripheral portion of outer face 146a is cut away to provide an outer annular recess 146b which exposes the inner surface 124 of acetabular shell component 112 at open end 122 thereof. Two parallel spaced circumferential grooves 170 and 172 are formed in inner surface 124 within recess 146b.

In addition, rim insert 148 is formed with an annular boss 148d extending upwardly from inner planar surface 148a and spaced inwardly from the outer peripheral edge of rim insert 148 so as to define an annular peripheral section 148e of rim insert 148. Annular boss 148d, as shown in FIG. 6, has a substantially rectangular cross-sectional configuration, and is formed with two spaced annular beads or ribs 148f and 148g on the outwardly facing surface thereof, ribs 148f and 148g being dimensioned and positioned to engage within grooves 170 and 172 so as to removably secure rim insert 148 to acetabular shell component 112.

As shown in FIG. 7, rim insert 148 has a slit-like opening 148h extending therethrough such that rim insert 148 effectively functions as a split ring. As a result, rim insert 148 can be compressed such that opposite edges 148i and 148j of slit-like opening 148h can be moved toward each other, whereby ribs 148f and 148g can be removed from grooves 170 and 172 so as to remove rim insert 148 from acetabular shell component 112. In order to accomplish such compression, rim insert 148 is provided with two hemostat holes 148k on opposite sides of slit-like opening 148h which permits insertion of a hemostat or other similar surgical instrument to compress rim insert 148 to effect removal or retraction of rim insert 148 from acetabular shell component 112 and bearing insert 146.

Further, annular peripheral section 148e, extending to the outside of boss 148d, has a plurality of gear teeth or locking splines 148l formed thereabout in facing relation to open circumferential end 122 of acetabular shell component 112. In like manner, a plurality of gear teeth or locking splines 122a are formed at open circumferential end 122 of acetabular shell component 112 for mating engagement with locking splines 148l, and having the same pitch and dimensions as locking splines 148l. Preferably, as shown in FIG. 8, each locking spline occupies an angular pitch of 10°, although this can vary. Accordingly, when rim insert 148 is assembled with acetabular shell component 112 as shown in FIG. 6, locking splines 122a and 148l are in mating engagement so as to prevent rotation of rim insert 148, and thereby to lock rim insert 148 at a desired angular orientation. With the aforementioned 10° angular pitch of the locking splines, it will be appreciated that there are 36 different possible orientations of socket insert 148.

Therefore, in order to change or adjust the angular orientation of rim insert 148, a hemostat or other similar surgical instrument is inserted within hemostat holes 148k in order to compress rim insert 148 so as to remove ribs 148f and 148g from grooves 170 and 172. Thereafter, rim insert 148 is pulled away from socket insert 146, and the compressive force on rim insert 148 is removed.

Figure 11:
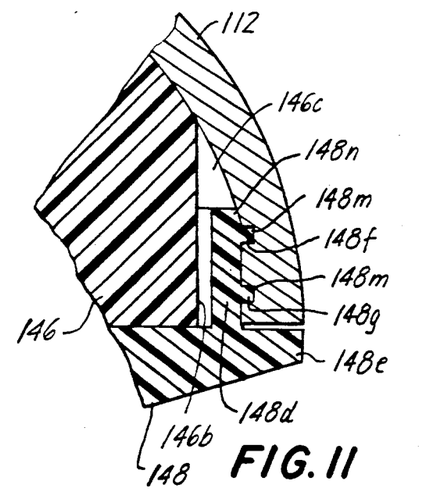
FIG. 11 is a cross-sectional view of a portion of a modified version of the implantable prosthetic hip joint of FIG. 6.
Figure 12:
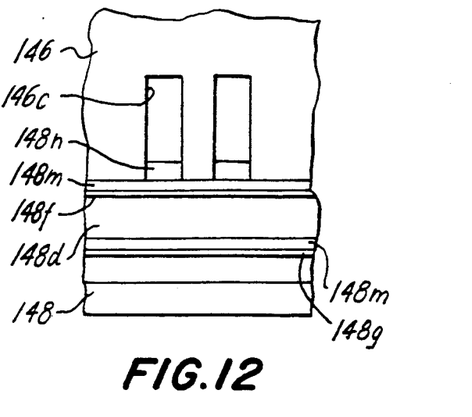
FIG. 12 is an elevational view of a portion of the implantable prosthetic hip joint of FIG. 11.

Upon continued removal of rim insert 148, rib 148f will locate within groove 172, as shown in FIG. 10. In this condition, rim insert 148 will still be locked to acetabular shell component 112. However, locking splines 122a and 148l will be out of engagement so as to permit rotation of rim insert 148. When rim insert 148 is rotated to the desired angular orientation, it is again compressed and pushed toward socket insert 146 until ribs 148f and 148g are engaged within grooves 170 and 172. Therefore, both locking ribs 148f and 148g are engaged in locking grooves 170 and 172 within acetabular shell component 112 to effect a redundant and retentive locking function. Furthermore, the rotational position of socket face 148b is maintained in a fixed orientation by engagement of the locking splines. As an alternative embodiment, locking ribs 148f and 148g can each be provided with an upper beveled surface 148m, as shown in FIGS. 11 and 12. With this arrangement, in order to move rim insert 148 from the position shown in FIG. 10 (or a totally removed position) to that shown in FIG. 6, it is merely necessary to push rim insert 148 toward bearing insert 146, whereby beveled edges 148m of locking ribs 148f and 148g will slightly compress rim insert 148.

In addition, as shown in FIGS. 11 and 12, spline tabs 148n can be provided, extending in spaced relation at the upper end of annular boss 148d, preferably with the same pitch as locking splines 148l for receipt in spline grooves 146c having the same pitch. As a result, spline retentive function along with the locking splines. It will be appreciated that spline tabs 148n and spline grooves 146c can be provided, alternatively, in place of the locking splines.

It will be appreciated that, with the embodiments of FIGS. 6-12, unlike the embodiment of FIGS. 1-5, angular orientation can be provided in a plurality of discrete orientations, rather than the universal angular positioning provided in the embodiment of FIGS. 1-5.

Figures 13, 14, 14A:
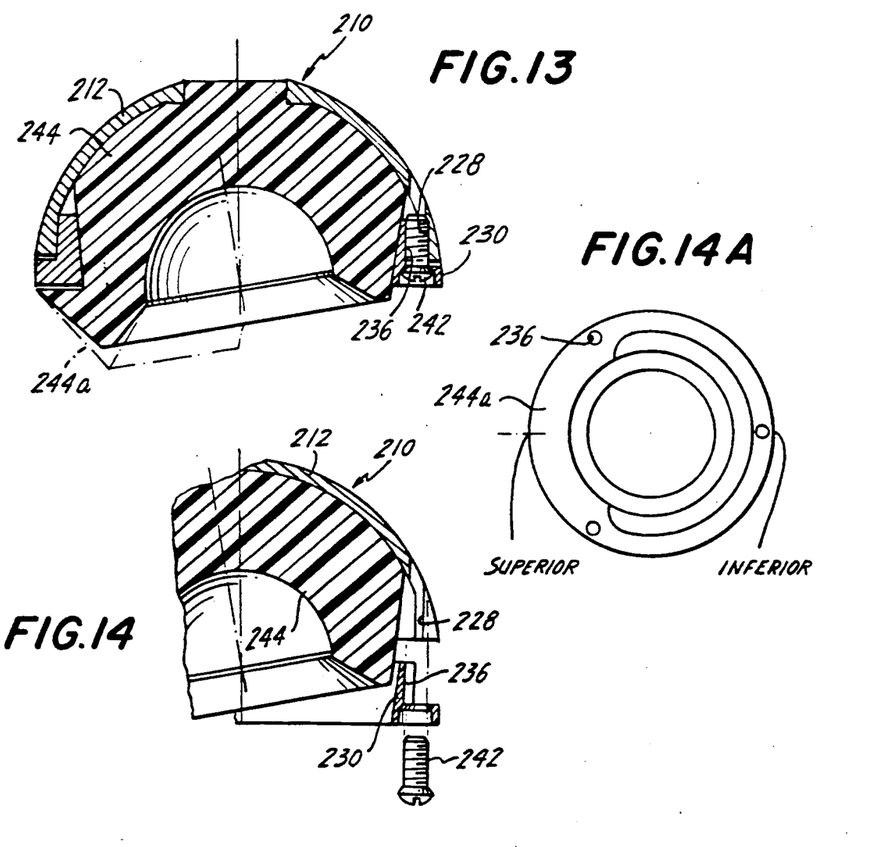
FIG. 13 is a cross-sectional view of an implantable prosthetic hip joint according to another embodiment of the present invention.
FIG. 14 is a cross-sectional view similar to FIG. 13, of a portion of the implantable prosthetic hip joint shown in an unassembled condition.
FIG. 14A is a bottom plan view of the implantable prosthetic hip joint of FIG. 13.

Referring now to FIGS. 13 and 14, an implantable prosthetic hip joint 10 according to another embodiment of the present invention will now be described in which elements corresponding to those described with respect to the above embodiments, are identified by the same reference numerals with a 200 prefix, and a detailed description of the common elements will be omitted herein for the sake of brevity.

Specifically, with implantable prosthetic hip joint 210, the locking or wedging force for retaining socket insert 244 within acetabular shell component 212 is derived from cap screws 242 rather than the cancellous bone screws 42 in the embodiment of FIGS. 1-5. This is because some orthopedic surgeons strongly prefer not to use bone screws 42 for securing or for augmenting fixation of the acetabular shell component. Therefore, the use of cap screws 242 in the present embodiment of FIGS. 13 and 14 is provided to address this surgical preference. Thus, the holes 228 in acetabular shell component 212 are partially threaded. For a wedge retaining ring 230 of titanium alloy construction, a plurality of corresponding holes of sufficiently large diameter to provide clearance engagement with the inserted cap screws 242, are provided. To augment retention of cap screws 242 within the partially threaded holes, it is preferable that cap screws 242 be provided with a UHMWPE lock insert (not shown). For a wedge retaining ring 230 of UHMWPE construction, the mating integral hole pattern will consist of a series of interference or partial holes 236, equal to the pitch diameter of cap screws 242, to provide additional retention capability.

Further, as shown in FIG. 14A, the superior portion of socket insert 244 can be "hooded" or incorporate an extended roof 244a, to provide additional acetabular socket stability. In this type of design, a slit wedge retaining ring 230 will facilitate assembly with socket insert 244. The superior hooded portion 244a is also shown in dashed lines in FIG. 13.

As with implantable prosthetic hip joint 10 of FIGS. 1-5, implantable prosthetic hip joint 210 features a wide range of socket face orientation positional adjustment, a wedge-type of socket insert securement within the acetabular shell component, and relative ease and facility of repositioning the socket face orientation, when interoperative prosthetic hip joint stability parameters dictate.

Referring now to FIGS. 15-19, an implantable prosthetic hip joint 310 according to another embodiment of the present invention will now be described, in which elements corresponding to those identified with respect to previously described prosthetic hip joints are identified by the same reference numerals with a 300 prefix, and a detailed description of the common elements will be omitted herein for the sake of brevity.

Figures 15, 19:
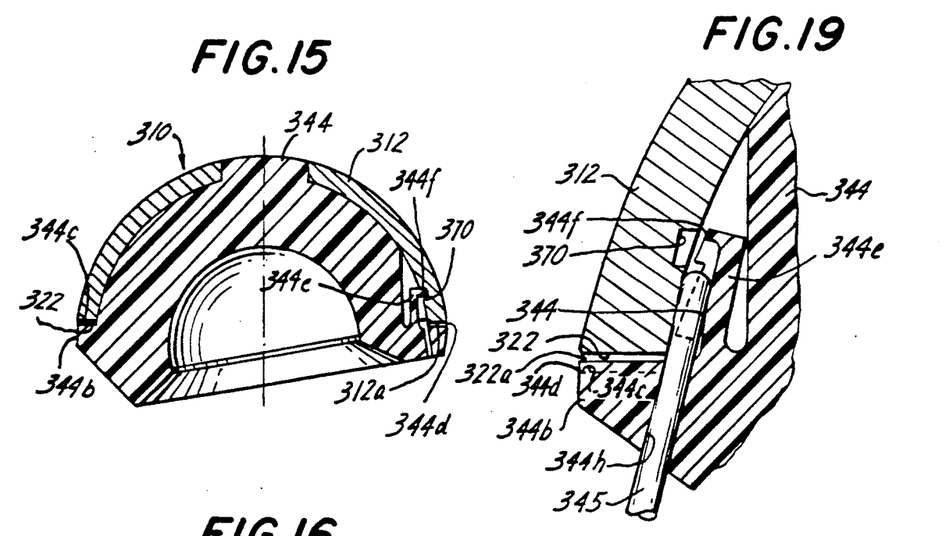
FIG. 15 is a cross-sectional view of an implantable prosthetic hip joint according to another embodiment of the present invention.
FIG. 19 is an enlarged cross-sectional view of the implantable prosthetic hip joint of FIG. 17, showing a locking tab in a disengaged condition.
Figure 16:
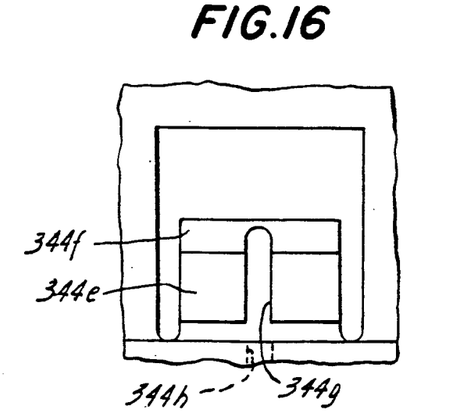
FIG. 16 is an elevational view of a locking tab of the implantable prosthetic hip joint of FIG. 15.
Figure 17:
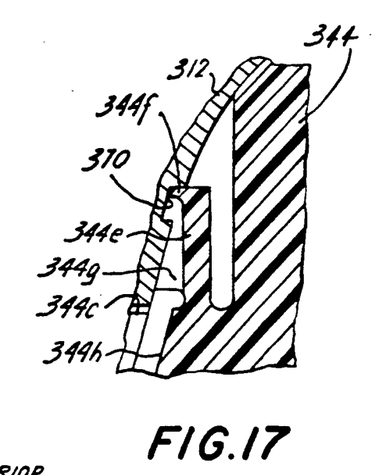
FIG. 17 is an enlarged cross-sectional view of the locking tab in assembled condition.

Specifically, socket insert 344 is formed with an annular rim section 344b having an upper surface 344c which mates with open circumferential end 322 of acetabular shell component 312. Further, locking splines 344d are provided on upper rim surface 344c in much the same manner as locking splines 148l and mating locking splines 322a are provided at open circumferential end 322 of acetabular shell component 312 so as to mate therewith during final seating of socket insert 344 within acetabular shell component 312, to provide rotational constraint. Of course, the range of positional adjustment of the socket face is related to the pitch of the locking splines and the outside diameter of acetabular shell component 312. For example, a 50 mm outer diameter acetabular shell component 312 with a locking spline pitch of 3.019 mm will provide a total of 52 positional increments of adjustment.

In order to removably lock socket insert 344 to acetabular shell component 312, socket insert 344 is cut away to provide several equiangularly spaced locking tabs 344e machined integral to socket insert 344. Each locking tab 344e includes a locking key 344f which extends radially outward and engages within a mating groove 370 machined around the inner periphery of acetabular shell component 312 and located adjacent to open circumferential end 322 thereof. Each locking tab 344e incorporates a rod channel 344g on its front face to accept a removal rod 345, as shown in FIG. 19, to facilitate interoperative socket insert removal from acetabular shell component 312. At each locking location, removal rod 345 is inserted into an available port 344h in socket insert 344, which forms a continuation of groove 344g. As a result, removal rod 345 pushes against the inner surface of acetabular shell component 312 and the front face of locking tab 344e. The wedging force created thereby causes locking tab 344e to pivot inwardly, thereby disengaging locking key 344f from groove 370. This operation is performed concurrently for all locking tabs 344e in order to remove socket insert 344.

In situations where orientation of the socket face has to be repositioned because of joint stability considerations, removal rods 345 are inserted to disengage locking keys 344e, as described above. Socket insert 344 can then be rotated to a more stable position and reevaluated by passively moving the hip joint through a complete range of motion. Once stability has been verified, removal rods 345 can be withdrawn to relock socket insert 344 in position.

Figure 18:
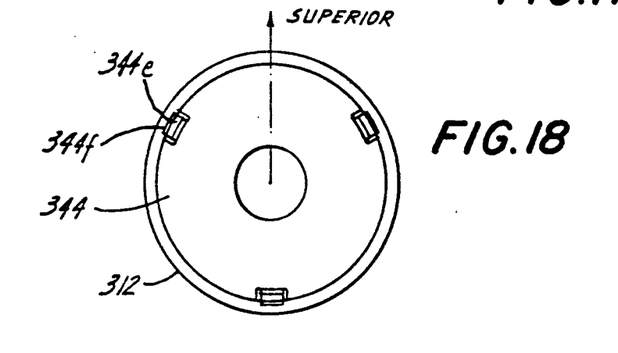
FIG. 18 is a top plan view of the implantable prosthetic hip joint of FIG. 15 without the acetabular shell component.

Preferably, three or four equiangularly spaced locking tabs 344e can be utilized for socket insert securement. However, such tabs 344e should preferably not be positioned within the superior portion of socket insert 344, as shown in FIG. 18, since this region is consistent with the major weight-bearing plane of the hip joint. Therefore, maximum thickness of UHMWPE material is available within the weight-bearing sector of acetabular shell component 312, which is desirable from long-term functional considerations.

Referring now to FIGS. 20–23, an implantable prosthetic hip joint 410 according to another embodiment of the present invention will now be described in which elements corresponding to those in the previously described embodiments are identified by the same reference numerals with a 400 prefix, and a detailed description of the common elements thereof will be omitted herein for the sake of brevity.

Figure 20:
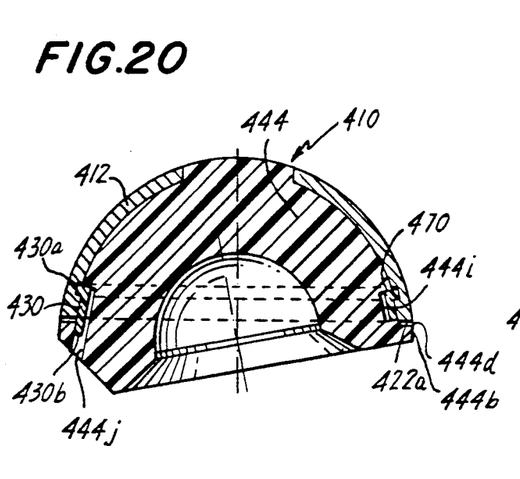
FIG. 20 is a cross-sectional view of an implantable prosthetic hip joint according to another embodiment of the present invention.

Socket insert 444 is provided with a rim section 444b having locking splines 444d thereon which mate with locking splines 422a of acetabular shell component 412 when socket insert 444 is assembled therewith, to lock socket insert 444 in a predetermined angular orientation.

Socket insert 444 further includes an annular ring groove 444i having a ring access port 444j to permit access to ring groove 444i from the outside.

Figures 21, 23, 24:
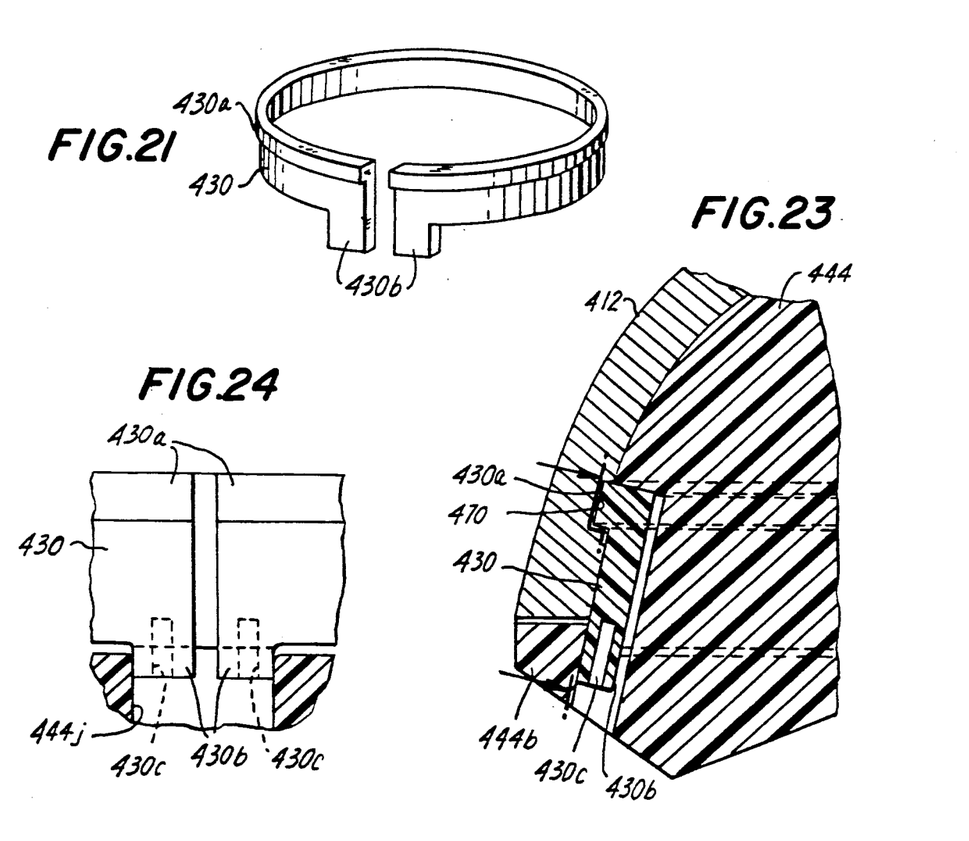
FIG. 21 is a perspective view of the retaining ring thereof.
FIG. 23 is an enlarged cross-sectional view showing engagement of the retaining ring with the acetabular shell component.
FIG. 24 is a partial cross-sectional view, showing positioning of the locking tangs of the retaining ring within the ring access port.
Figure 22:
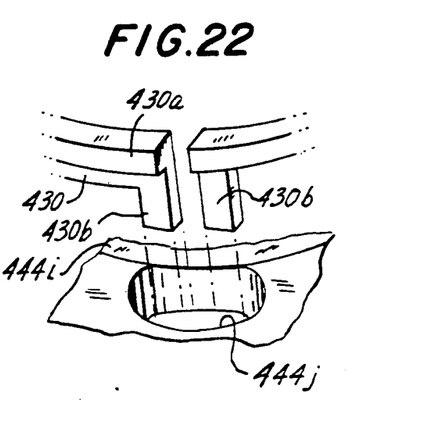
FIG. 22 is a perspective view showing assembly of the locking tangs of the retaining ring for positioning in the ring access port.

A split annular retaining ring 430 is positioned within ring groove 444i and includes an outwardly radial directed locking rib 430a which engages within an annular groove 470 in the inner surface of acetabular shell component 412. Retaining ring 430 is preferably a UHMWPE ring. As a result, a secure locking function of socket insert 444 is achieved in acetabular shell component 412, while rotational orientation thereof is fixed by the locking splines.

Retaining ring 430 further includes downwardly extending removal tangs 430b which occupy positions within ring access port 444j in socket insert 444. The lower face of each removal tang 430b is provided with a spanner hole 430c, as best shown in FIGS. 23 and 24. In the assembled condition, spanner holes 430c at the ends of removal tangs 430b are visible and accessible through ring access port 444j. Accordingly, socket insert 444 can be readily removed from acetabular shell component 412 by inserting a hemostat or other similar surgical instrument through ring access port 444j, and engaging spanner holes 430c so as to compress split retaining ring 430 in order to disengage locking ribs 430a from groove 470 in acetabular shell component 412. It will be appreciated that the ease and facility of socket insert removal from acetabular shell component 412 is an essential feature to allow ease of interoperative modification of socket face orientation, when final evaluation of the stability of prosthetic hip joint 410 dictates, and also for removal and replacement of socket insert 444 during revision surgery situations.

Referring now to FIGS. 25–30, an implantable prosthetic hip joint 510 according to another embodiment of the present invention will now be described in which elements corresponding to those in the previously described embodiments are identified by the same reference numerals with a 500 prefix, and a detailed description of the common elements thereof will be omitted herein for the sake of brevity.

Figures 25, 29:
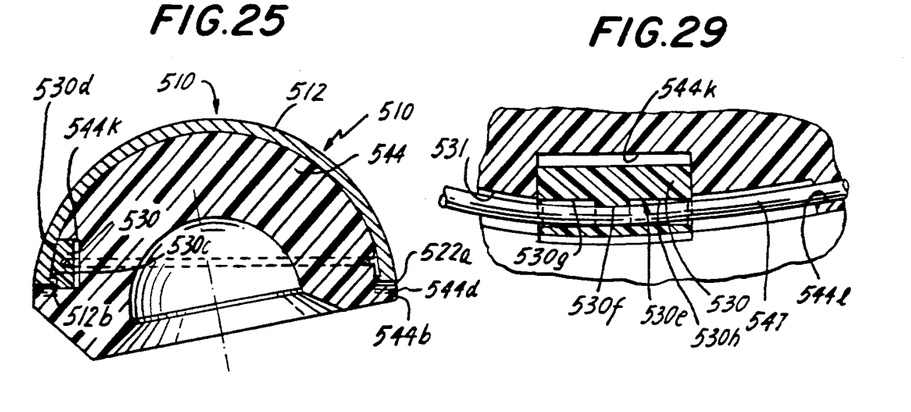
FIG. 25 is a cross-sectional view of an implantable prosthetic hip joint according to another embodiment of the present invention.
FIG. 29 is a cross-sectional view of a locking pellet in assembled condition, taken along line 29—29 of FIG. 28.
Figure 26:
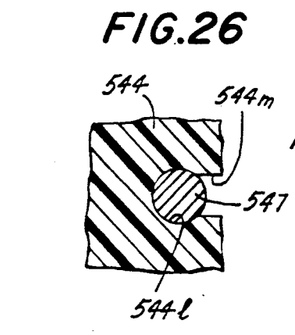
FIG. 26 is an enlarged cross-sectional view of the portion of the implantable prosthetic hip joint of FIG. 25, showing the channel in the socket insert.
Figure 27:
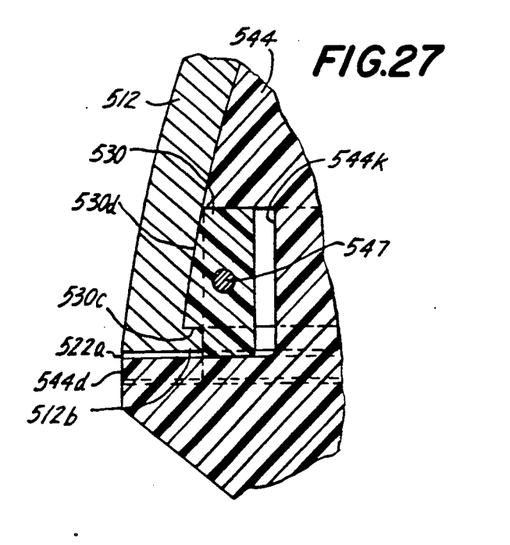
FIG. 27 is an enlarged cross-sectional view of a portion of the implantable prosthetic hip joint of FIG. 25, showing a locking pellet in assembled condition.
Figure 28:
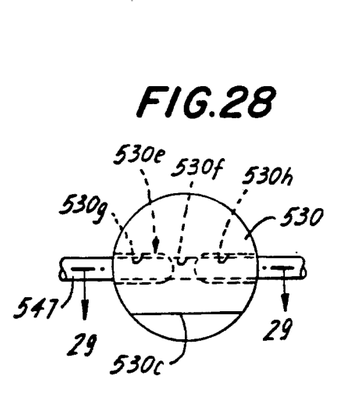
FIG. 28 is a front elevational view of a locking pellet.

Specifically, socket insert 544 is provided with a plurality, for example, three or four, of pellet recesses 544k equiangularly spaced thereabout, and acetabular shell component 512 is provided with an inwardly turned circumferential locking ledge 512b extending into each recess 544k. A locking pellet 530 is positioned within each recess 544k and includes a locking shoulder 530c for engagement with the locking ledge 512b so as to retain socket insert 544 within acetabular shell component 512 such that the locking splines 544d and 522a are in locking engagement with each other. It will be appreciated that the outer face 530d of each locking pellet 530 is inclined downwardly and outwardly toward shoulder 530c, as shown. Locking pellet 530 is preferably fabricated of UHMWPE and is of a cylindrical configuration, which simplifies manufacturing thereof.

A bore 530e extends through each locking pellet 530 in the circumferential direction of socket insert 544, the mid-section 530f of bore 530e being of smaller diameter than the outer portions 530g and 530h of the bore. A clearance channel 531 is provided for a portion of the annular surface of socket insert 544 adjacent each recess 544k and is formed essentially as a continuation of bore 530e. In addition, socket insert 544 includes a wire channel 544l extending therearound as a continuation of clearance channel 531 and having a clearance opening 544m. As a result, a circumferential wire 547 of titanium alloy or cobalt-chrome alloy, is contained within wire channel 544l located just under the surface of socket insert 544 and also extends within clearance channel 531 and each bore 530e, with a tight fit within mid-section 530f thereof. Wire 547 is of a split loop configuration. Pellets 530 are strung on wire 547 and then installed in the respective recesses 544k when wire 547 is assembled into wire channel 544l. As a result, smooth displacement of each locking pellet 530 is accomplished during engagement and disengagement functions. Wire channel 544l is specially machined, using a ball end mill, to provide a tight fit with wire 547 and to allow peripheral slippage of the wire during locking and unlocking displacements of locking pellets 530.

Figure 30:
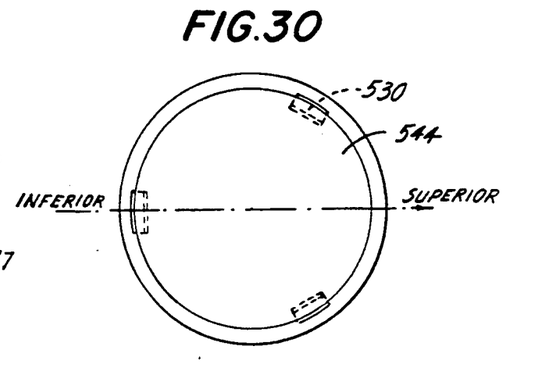
FIG. 30 is a top plan view of the implantable prosthetic hip joint of FIG. 25, without the acetabular shell component.

Locking pellets 530, which preferably number three or four, are strategically placed about the periphery of socket insert 544, purposefully avoiding the superior or weight-bearing region of the acetabulum. In this manner, maximum available thickness of UHMWPE bearing material is provided, which is desirable from the standpoint of long-term clinical use. In this manner, spring wire 547 provides a spring force to lock pellets 530 for maintaining locking engagement with integral mating groove 570 in acetabular shell component 512, and also functions as a radiographic identification of inadvertent socket insert disassembly.

Unfortunately, this construction does not provide an unlocking feature, but is considered to be inherently more reliable and less likely to jam, as well as providing a wider range of socket face orientation positional adjustment than known arrangements.

Referring now to FIGS. 31–34, an implantable prosthetic hip joint 610 according to another embodiment of the present invention will now be described in which elements corresponding to those in the previously described embodiments are identified by the same reference numerals with a 600 prefix, and a detailed description of the common elements thereof will be omitted herein for the sake of brevity.

Figure 31:
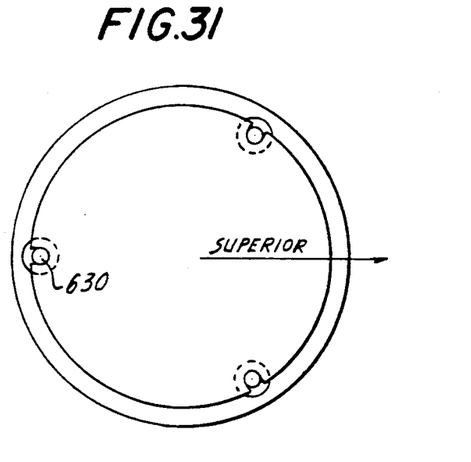
FIG. 31 is a top plan view of an implantable prosthetic hip joint according to another embodiment of the present invention, without the acetabular shell component.

Specifically, prosthetic hip joint 610 is similar to prosthetic hip joint 510. However, locking pellets 630 are each provided with a circumferential groove 630e which receives spring wire 647. In addition, each recess 664k of socket insert 644 is provided with a cut-away ledge 644n which is configured to receive shoulder 630c of the respective locking pellet 630. Each locking pellet 630 is rotatably positioned within slotted recess 644k between the locking position of FIG. 32 to the unlocking position of FIG. 33.

Further, each slotted recess 644k includes an access port 644j. The cylindrical lower portion 630i of each locking pellet 630 is provided with a slot 630j for receipt of a screwdriver or similar instrument in order to rotate each locking pellet 630 between the positions of FIGS. 32 and 33. It will be appreciated that, in the position of FIG. 32, the lower end 630k of each locking pellet 630 is machined at a bias to be flush with the lower face of socket insert 644, but in the unlocked position of FIG. 33, the cylindrical end of each locking pellet 630 will protrude beyond the boundary of the chamfered socket face surface, thus functioning as a visual indication of the unlocked position.

Figure 32:
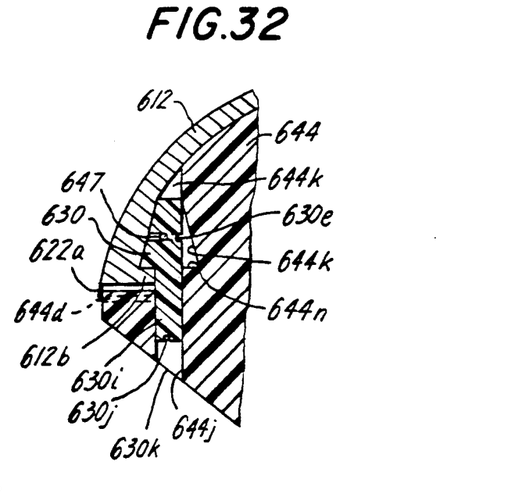
FIG. 32 is an enlarged cross-sectional view of a portion of the implantable prosthetic hip joint of FIG. 31, showing a locking pellet thereof in an operative condition.
Figure 33:
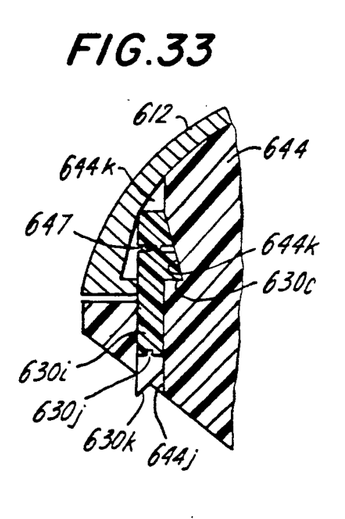
FIG. 33 is a cross-sectional view similar to FIG. 32, showing the locking pellet in an inoperative condition.

In the locked position of FIG. 32, locking splines 644d and 622a are in mating relation so as to provide rotational constraint and thereby to permit selection and maintenance of a wide range of socket face orientation positions. For socket insert removal in the event of socket face orientation adjustment or replacement during surgical revision, it is only necessary to rotate locking pellets 630 to the unlocked position of FIG. 33 and either remove and/or rotate socket insert 644.

Figures 34, 36:
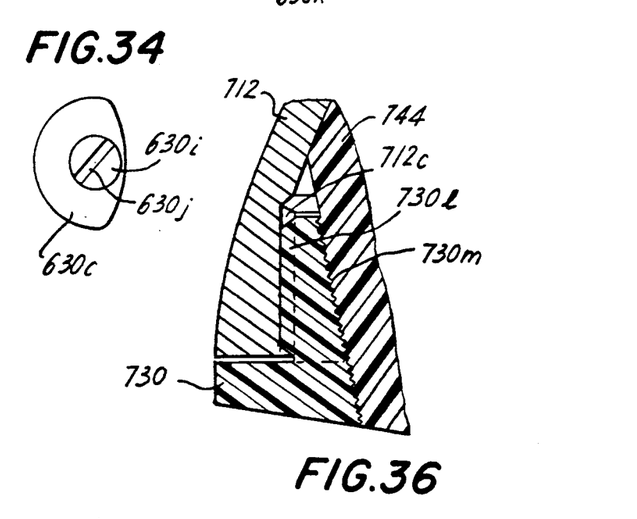
FIG. 34 is a bottom plan view of a locking pellet.
FIG. 36 is an enlarged cross-sectional view of a modified version of the implantable prosthetic hip joint of FIG. 35, showing serrations on the wedge retaining ring.
Figure 35:
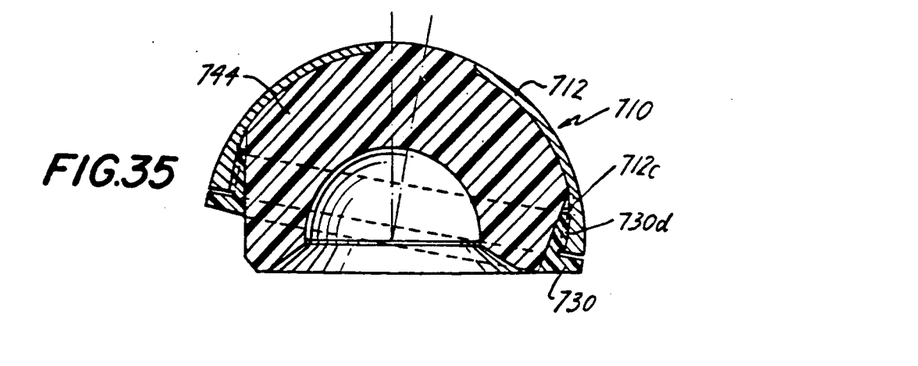
FIG. 35 is a cross-sectional view of an implantable prosthetic hip joint according to another embodiment of the present invention.

Referring now to FIGS. 35 and 36, an implantable prosthetic hip joint 710 according to another embodiment of the present invention will now be described in which elements corresponding to those in the previously described embodiments are identified by the same reference numerals with a 700 prefix, and a detailed description of the common elements thereof will be omitted herein for the sake of brevity.

Specifically, prosthetic hip joint 710 is similar to that of FIGS. 1-5 which provides an infinite number of socket face orientations. However, in place of screws 42, wedge retaining ring 730 is screw threaded to acetabular shell component 712. Specifically, screw threads 730l on wedge retaining ring 730, which is machined from UHMWPE, titanium or cobalt-chrome alloys, matingly engages with threads 712c on the inner surface of acetabular shell component 712.

In addition, the conical or tapered locking surface 730m of wedge retaining ring 730 at the ring/socket insert interface, can be machined with a closed or spiraled serrated pattern, as shown in FIG. 36, to provide additional locking capability. Therefore, in order to change the angular orientation of socket insert 744, it is only necessary to unscrew wedge retaining ring 730 a small amount, then rotate socket insert 744 to the correct angular orientation, and finally thread wedge retaining ring 730 back into acetabular shell component 712 in a tight manner so as to lock socket insert 744 thereto.

It will therefore be appreciated that, with all of the above embodiments, an implantable prosthetic hip joint is provided that has numerous angular orientations, with a 360° adjustability. Further, the manner of adjustment of the angular orientation of the socket insert bearing face is easily provided interoperatively or postoperatively.

Having described specific preferred embodiments of the invention with reference to the accompanying drawings, it will be appreciated that the present invention is not limited to those specific embodiments, and that various changes and modifications can be effected therein by one of ordinary skill in the art without departing from the scope or spirit of the invention as defined by the appended claims.

What is claimed is:

1. An implantable prosthetic joint comprising:
   a) first bone securing means for constraining said prosthetic joint within a fist bone of a biological joint, said first bone securing means including a spherical shell securable within a socket of said first bone, said shell including an inner spherical surface and an open circumferential end;
   b) second bone securing means for securing the prosthetic joint to a second bone of the biological joint, said second bone securing means including a femoral head and stem means connected with said femoral head for securing the prosthetic joint to the second bone;
   c) asymmetric socket insert means for connecting said second bone securing means with said first bone securing means, said socket insert means including:
      i) an outer spherical dome which engages with the inner spherical surface of said shell;
      ii) an open circumferential end having an asymmetric lip thereat; and
      iii) an inner spherical surface which receives said femoral head for ball-and-socket movement therein;
   d) wedge-shaped means, interposed between said socket insert means and said first been securing means, for applying a radially inward force component on said socket insert means to releasably secure said socket insert means in a non-rotatable manner with respect to said first bone securing means; and
   e) securing means, out of engagement with said socket means, for releasably securing said wedge means to said first bone securing means such that said socket insert means is assembled with said first bone securing means in a fixed and immovable manner, while providing infinite angular adjustability of said socket means with respect to said first bone securing means when said securing means releases said wedge means from said first bone securing means.

2. An implantable prosthetic joint comprising:
   a) first bone securing means for constraining said prosthetic joint with a first bone of a biological joint, said first bone securing means including a spherical shell securable within socket of said first bone, said shell including an inner spherical surface and an open circumferential end;
   b) second bone securing means for securing the prosthetic joint to a second bone of the biological joint, said second bone securing means including a femoral head and stem means connected with said femoral head for securing the prosthetic joint to the second bone;
   c) asymmetric socket insert means for connecting said second bone securing means with said first bone securing means, said socket insert means including:

i) an outer spherical dome which engages with the inner spherical surface of said shell;

ii) an open circumferential end having an asymmetric lip thereat; and iii) an inner spherical surface which receives said femoral head for ball-and-socket movement therein;

d) wedge-shaped means, interposed between said socket insert means and said first bone securing means, for releasably securing said socket insert means in a non-rotatable manner with respect to said first bone securing means; and e) securing means, out of engagement with said socket means, for releasably securing said wedge means to said first bone securing means such that said socket insert means is assembled with said first bone securing means in a fixed and immovable manner, while providing infinite angular adjustability of said socket means with respect to said first bone securing means when said securing means releases said wedge means from said first bone securing means, said securing means including:

i) a plurality of apertures extending through said wedge means;

ii) a plurality of apertures extending through the open circumferential end of said spherical shell in alignment with said apertures through said wedge means; and iii) screw means, insertable said apertures of said wedge means and said spherical shell, for forcing said wedge means between said socket insert means and said first bone securing means, so as to lock said socket insert means to said first bone securing means in a predetermined orientation, whereby loosening of said screw means permits rotational adjustment of said socket insert means in said spherical shell in any of an infinite number of angular orientations.

3. A implantable prosthetic joint according to claim 2, wherein said screw means includes a plurality of cancellous bone screws.

4. An implantable prosthetic joint according to claim 2, wherein said screw means includes a plurality of cap screws.

5. An implantable prosthetic joint according to claim 2, wherein said apertures in said wedge means and said spherical shell are arranged circumferentially about said implantable prosthetic joint.

6. An implantable prosthetic joint according to claim 2, wherein said wedge means includes an annular wedge wall interposed between the socket insert means and the first bone securing means and an annular flange connected with an outer end of said annular wedge wall, said flange being radially directed outwardly from said annular wedge wall, and said plurality of apertures in said wedge means being formed through said flange.

7. An implantable prosthetic joint according to claim 6, wherein said apertures in said annular flange are counter-sunk.

8. An implantable prosthetic joint according to claim 1, wherein said outer spherical dome includes an outer tapered surface for engagement with said wedge means.

9. An implantable prosthetic joint according to claim 1, wherein said outer spherical dome further includes shoulder means for preventing escape of said wedge means.

10. An implantable prosthetic joint according to claim 1, wherein said acetabular shell component includes a central hole and said socket insert means includes central key means inserted through said central hole for limiting movement of said socket insert means in said spherical shell in a rotatable manner about the axis of said central hole.

11. An implantable prosthetic joint according to claim 1, further including texturing on an outer surface of said spherical shell.

12. An implantable prosthetic joint according to claim 1, wherein said wedge means includes an annular wedge wall interposed between the socket insert means and the spherical shell, and said securing means includes first threads on an outer face of said annular wedge wall and second threads on the inner spherical surface of said spherical shell adjacent said open circumferential end for threadedly engaging with the first threads on said annular wedge wall so as to releasably secure said wedge means thereto.

13. An implantable prosthetic joint according to claim 1, wherein said wedge means includes an annular wedge wall interposed between the socket insert means and the spherical shell, said annular wedge wall including an inner inclined surface having serrations thereon for improving engagement of said wedge means with said socket insert means.

* * * * *